Figure 3A:
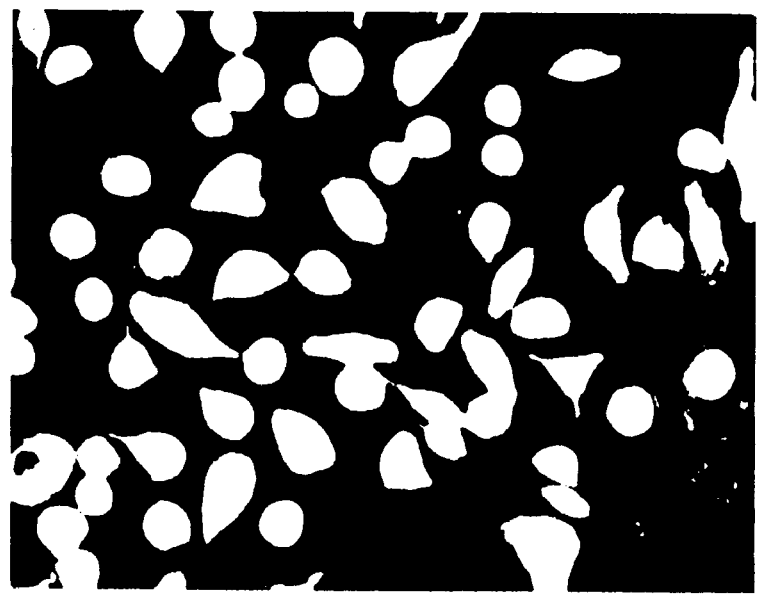

United States Patent [19]
Rabbani et al.

[11] Patent Number: 6,077,508
[45] Date of Patent: Jun. 20, 2000

[54] UROKINASE PLASMINOGEN ACTIVATOR RECEPTOR AS A TARGET FOR DIAGNOSIS OF METASTASES

[75] Inventors: Shafaat A. Rabbani, Westmount, Canada; Richard Hart, Greenwich, Conn.

[73] Assignees: American Diagnostica Inc., Greenwich, Conn.; McGill University, Montreal, Canada

[21] Appl. No.: 09/046,106

[22] Filed: Mar. 23, 1998

[51] Int. Cl.$^7$ .......................... G01N 33/53; A61K 39/395
[52] U.S. Cl. ......................... 424/174.1; 514/2; 530/387.1; 530/387.7; 530/387.9; 530/388.1; 530/388.15; 530/388.22; 424/9.6; 424/1.33; 424/1.69; 424/1.49
[58] Field of Search ..................................... 424/9.6, 1.11, 424/1.33, 1.37, 1.41, 1.49, 1.65, 1.69, 9.1, 9.2, 174.1; 435/4, 7.1, 7.7, 7.71, 7.72; 436/512, 547, 548; 514/2; 530/387.1, 387.7, 387.9, 388.1, 388.15, 388.22

[56] References Cited

U.S. PATENT DOCUMENTS

| | | |
|---|---|---|
| 4,782,840 | 11/1988 | Martin, Jr. et al. . |
| 5,015,571 | 5/1991 | Niman et al. . |
| 5,189,014 | 2/1993 | Cowan, Jr. . |
| 5,225,539 | 7/1993 | Winter . |
| 5,383,456 | 1/1995 | Arnold et al. . |
| 5,441,050 | 8/1995 | Thurston et al. . |
| 5,519,120 | 5/1996 | Danø . |
| 5,585,089 | 12/1996 | Queen . |
| 5,679,350 | 10/1997 | Jankun et al. . |

FOREIGN PATENT DOCUMENTS

| | | |
|---|---|---|
| 2246779 | 2/1992 | United Kingdom . |
| WO 92/02553 | 2/1992 | WIPO . |
| WO98/28145 | 12/1994 | WIPO . |

OTHER PUBLICATIONS

Rabbani, S.A. Urokinase receptor directed immunodiagnostic and immunotherapeutic strategies for prstate and breast cancer, Proceedings of the American Association for Cancer Research, vol. 38, p. 249, Mar. 21, 1997.

Andreasen et al., 1997, "The Urokinase–Type Plasminogen Activator System in Cancer Metastasis: A Review", Int. J. Cancer 72:1–22.

Appella et al., 1987, "The Receptor–Binding Sequence of Urokinase", J. Biol. Chem. 262:4437–4440.

Chucholowski et al., 1992, "Flow Cytofluorometric Analysis of the Urokinase Receptor (uPAR) on Tumor Cells by Fluorescent uPA–Ligand or Monoclonal Antibody #3936", Fibrinolysis 6(suppl. 4):95–102.

deVries et al., 1994, "Plasminogen Activators, Their Inhibitors, and Urokinase Receptor Emerge in Late Stages of Melanocytic Tumor Progression", Am. J. Path. 144:70–81.

Jankun et al., 1993, "Expression and Localization of Elements of the Plasminogen Activator System in Benign Breast Disease and Breast Cancers", J. Cell. Biochem. 53:135–144.

Jankun, 1993, "The Urokinase Plasminogen Activator Pathway as a Novel Mechanism of Tumor Targeting and Cell Membrane Traversal", J. Cell. Biochem. Suppl. 17C:33 (abstr. H242).

Liotta et al., 1991, "Cancer Metastasis and Angiogenesis: An Imbalance of Positive and Negative Regulation", Cell 64:327–336.

Liotta, 1986, "Tumor Invasion and Metastases—Role of the Extracellular Matric: Rhoads Memorial Award Lecture", Cancer. Res. 46:1–7.

Mundy, 1997, "Mechanisms of Bone Metastasis", Cancer (suppl.) 80:1546–1556.

Presta et al., 1997, "Humanization of an Anti–Vascular Endothelial Growth Factor Monoclonal Antibody for the Therapy of Solid Tumors and Other Disorders", Cancer Res. 57:4593–4599.

Pyke et al., 1995, "Lamin–5 is a Marker of Invading Cancer Cells in Some Human Carcinomas and is Coexpressed with the Receptor for Urokinase Plasminogen Activator in Budding Cancer Cells in Colon Adenocarcinomas", Cancer Res. 55:4132–4139.

Rabbani, 1997, "Urokinase Receptor Directed Immunodiagnostic and Immunotherapeutic Strategies for Prostate and Breast Cancer", Proc. Am. Assoc. Cancer Res. 38:249 (abstr. 1673).

Rabbani et al. 1994, "Isolation and Characterization of Multiple Isoforms of the Rat Urokinase Receptor in Osteoblasts", FEBS Lett. 338:69–74.

Rabbani et al., 1992, "Structural Requirements for the Growth Factor Activity of the Amino–Terminal Domain of Urokinase", J. Biol. Chem. 267:14151–14156.

Schmitt et al., 1997, "Clinical Impact of the Plasminogen Activation System in Tumor Invasion and Metastasis: Prognostic Relevance and Target for Therapy", Thrombosis and Haemostasis 78:285–296.

Will et al., 1994, "Expression of Urokinase–type Plasminogen Activator (uPA) and Its Receptor (uPAR) in Human Ovarian Cancer Cells and in vitro Invasion Capacity", Intl. J. Oncology 5:753–761.

Xing and Rabbani, 1996, "Role of Urokinase Receptor in Breast Cancer Invasion and Metastasis: Potential Therapeutic Strategies", Proc. Am. Assoc. Cancer Res. 37:90 (abstr. 626).

Xing and Rabbani, 1996, "Overexpression of Urokinase Receptor in Breast Cancer Cells Results in Increased Tumor Invasion, Growth and Metastasis", Int. J. Cancer 67:423–429.

*Primary Examiner*—Julie Burke
*Attorney, Agent, or Firm*—Pennie & Edmonds LLP

[57] ABSTRACT

The present invention relates to the use of molecules capable of specifically binding a urokinase plasminogen activator receptor (uPAR) as diagnostic reagents for the detection of metastases in vivo. Such metastases can include, but are not limited to, micrometastases.

17 Claims, 8 Drawing Sheets

Val Pro Ser Asn Cys Asp Cys Leu Asn Gly Gly Thr Cys Val Ser Asn
7                  13                16                  21
Lys Tyr Phe Ser Asn Ile His Trp Cys Asn Cys
26                          31

FIG.1

Asp Cys Leu Asn Gly Gly Thr Cys Val Ser Asn
12                       16                 20
Lys Tyr Phe Ser Asn Ile His Trp Cys Asn Cys
26                              33

FIG.2

UROKINASE PLASMINOGEN ACTIVATOR RECEPTOR AS A TARGET FOR DIAGNOSIS OF METASTASES

1. INTRODUCTION

The present invention relates to the use of molecules capable of specifically binding a urokinase plasminogen activator receptor (uPAR) as diagnostic reagents for the detection of metastases. Such metastases can include, but are not limited to, micrometastases.

2. BACKGROUND

Cancer cell invasion and metastasis is a multistep process involving several interdependent processes (Liotta, 1986, Cancer Res. 46:1–7; Liotta et al., 1991, Cell 64:327–336; Mundy, 1997, Cancer 80(9):1546–1556). Metastasis, the growth of secondary tumors at sites distant from a primary tumor, is the major cause of failures of cancer treatment.

2.1. THE METASTATIC PROCESS

The regulatory mechanisms involved in metastases differ from those that cause tumor formation. In fact, metastatic cells appear to be physiologically different than tumor cells. For example, metastatic cells differ in expression of genes such as ras oncogene, serine-threonine kinases, tyrosine kinases, and p53 as well as differ in signal transduction (for review see Liotta et al., 1991, Cell 64:327–336).

Prior to metastasis, expansion of a tumor involves angiogenesis, the formation of new blood vessels (Folkman et al., 1989, Nature 339:58–61). Tumors have been shown to induce angiogenesis through several soluble factors (Folkman et al., 1987, Science 235:442–447; Pepper et al., 1990, J. Cell Biol. 111:743–755). Angiogenesis is a multistep process emanating from microvascular endothelial cells. Endothelial cells resting in parent vessels are stimulated to degrade the endothelial basement membrane, migrate into the perivascular stroma, and initiate a capillary sprout (Liotta et al., 1991, Cell 64:327–336). The capillary sprout subsequently expands and assumes a tubular structure. Endothelial proliferation leads to extension of the microvascular tubules, which develop into loops and then into a functioning circulatory network. The exit of endothelial cells from the parent vessel involves cell migration and degradation of the extracellular matrix (ECM) in a manner similar to cancer cell invasion of the ECM (Liotta et al., 1991, Cell 64:327–336).

Cancer cell invasion involves interactions of cancer cells with the ECM, a dense latticework of collagen and elastin embedded in a gel-like ground substance composed of proteoglycans and glycoproteins. The ECM consists of the basement membrane and its underlying interstitial stroma. Tumor invasion involves: (1) cancer cell detachment from their original location; (2) attachment to the ECM; (3) degradation of the ECM; and (4) locomotion into the ECM (for review see Liotta, 1986, Cancer Res. 46:1–7). Following detachment of the cancer cells, the cells migrate over the ECM and adhere to components of the ECM such as laminin, type IV collagen and fibronectin via cell surface receptors. Cell adhesion molecules, such as integrin, have been shown to mediate cancer cell attachment to vascular endothelial cells and to matrix proteins (Mundy, 1997, Cancer 80(9):1546–1556). The attached cancer cell then secretes hydrolytic enzymes or induces host cells to secrete enzymes which locally degrade the matrix. Matrix lysis occurs in a highly localized region close to the cancer cell surface, where the amount of active enzyme outbalances the natural proteinase inhibitors present in the serum, in the matrix, or that secreted by normal cells in the vicinity (Liotta et al., 1991, Cell 64:327–336). A positive association with tumor aggressiveness has been noted for various classes of degradative enzymes, including: heparinases, thiol-proteinases (including cathepsins B and L), metalloproteinases (including collagenases, gelatinases, and stromelysins), and serine proteinases (including plasmin and urokinase plasminogen activator).

During the locomotion step of invasion, cancer cells migrate across the basement membrane and stroma through the zone of matrix proteolysis. The cancer cells then enter tumor capillaries (which arise as a consequence of specific angiogenic factors) and reach the general circulation via these capillaries. After traveling to distant sites of the organism, the intravasated cancer cells adhere to and extravasate through the vascular endothelium, and initiate new tumor formation, i.e., first forming a mass of cells that, via the angiogenesis process, becomes a vascularized tumor.

Thus, metastasis is not a simple, random process but rather is a multistep process dependent on specific properties of the tumor cells and supportive factors in the environment of the metastatic site.

2.2 IMPLICATION OF uPA AND uPAR IN THE METASTIC PROCESS AT THE PRIMARY TUMOR SITE

A large number of different molecules are involved in the metastatic process. Two examples of such molecules are uPA and its receptor, uPAR, which have been implicated in the tumor cell invasion aspect of the metastatic process. During cancer invasion, uPAR binds uPA released from surrounding cancer or stroma cells. Binding of uPA to its receptor focuses proteolytic action to the surface of cancer cells. uPA converts enzymatically inactive plasminogen into the serine protease, plasmin. Plasmin degrades many ECM proteins such as fibronectin, vitronectin, and fibrin thus facilitating ECM degradation, cancer cell proliferation, invasion, and metastasis (Schmitt et al., 1997, Thrombosis and Haemostasis 78(1):285–296). Plasmin can also catalyze activation of the zymogen forms of several metalloproteinases.

Studies have demonstrated that anti-uPA antibodies decrease tumor cell invasion and/or metastasis of cells from cultured tumor cell lines transplanted into animal models (for review seen Andreasen et al., 1997, Int. J. Cancer 72:1–22).

Several studies have been conducted to examine the therapeutic effect of substances that interact with components of the plasminogen activation pathway. Manipulation of the plasminogen activation pathway has resulted in decreased tumor growth rates (Jankun et al., U.S. Pat. No. 5,679,350 (injection of a medicament coupled to PAI-1 or PAI-2); Danø et al., U.S. Pat. No. 5,519,120 (injection of anti-uPA or anti-uPAR antibodies); and Xing and Rabbani, 1996, Proc. Amer. Assoc. Cancer Res. 37:90 (Abstract #626) (injection of anti-uPAR antibodies)). These studies indicate that uPAR plays a role in the initial stages of metastasis, i.e., tumor cell invasion.

Clinical findings have demonstrated that elevated levels of uPA, and the plasminogen activator, PAI-1, in primary tumor tissue are associated with poor prognosis of several cancers including cancer of the breast, cervix uteri, ovary, stomach, colon, lung, brain, kidney, bladder, and soft tissue (for review see Schmitt et al., 1997, Thrombosis and Haemostasis 78(1):285–296; Andreasen et al., 1997, Int. J.

Cancer 72:1–22). To a lesser extent, elevated levels of uPAR may also indicate poor prognosis (Schmitt et al., Thrombosis and Haemostasis 78(1):285–296).

2.3. DIAGNOSIS AND STAGING OF DISEASE

While detection of markers of metastatic disease at the primary tumor site may be useful for prognosis, and the design of therapeutic modalities, no reliable system currently exists for the detection of micrometastases in a patient—information which would be extremely important for staging disease and designing an appropriate clinical approach. Although metastatic tumors are derived from cells of the primary tumor, the metastatic tumors are considerably altered in their physiologic and growth characteristics, and need not express the same surface markers as the parental tumor cells. In fact, the inability to diagnose and image metastases, particularly micrometastases, in vivo, continues to be a major obstacle to the successful treatment of cancer.

Current surgical practice commonly resorts to vision and palpation in combination with locally determined protocols dictating the extent of tissue resection. Thus, tissue removed during surgery includes not only tissue suspected by the surgeon of being neoplastic, but also includes an amount of healthy tissue taken because the precise tumor margins and areas of micrometastasis cannot be readily ascertained by the surgeon. Moreover, isolated metastatic tissue distal to the primary tumor often cannot be readily detected by those commonly used methods. Accordingly, there is a great need in the art for sensitive methods to reliably detect and localize metastases in vivo.

3. SUMMARY OF THE INVENTION

The present invention relates to methods for the diagnosis and imaging of metastases using labeled molecules that specifically bind a urokinase plasminogen activator receptor, particularly for detecting and imaging metastases in vivo. The present invention is based, in part, on the Applicant's unexpected discovery, that antibodies directed against uPAR can be used to detect not only primary tumors in vivo but can be used to detect or image micrometastases and metastases at sites distal to the primary tumor. Metastatic tumors, while derived from cells of the primary tumor, are considerably altered in their physiologic and growth characteristics and need not express the same surface markers as parental primary tumors. Prior to the Applicant's discovery, uPA and uPAR had only been associated with primary tumors that exhibited metastatic properties. Moreover, uPA and uPAR are thought to be involved in the early steps of the metastatic process—i.e., in mobilizing cells out of a primary tumor. Thus, it was quite surprising to discover that cells distal to the primary tumor, which are engaged in establishing new tumors (i.e., via attachment—not mobilization—cell expansion, angiogenesis, etc.) can be detected using uPA or uPAR as a marker.

In a preferred embodiment of the invention, metastases in a subject are detected by: (a) administering labeled molecules which specifically bind uPAR; (b) permitting the labeled molecules to preferentially concentrate in one or more metastatic lesions in the subject and unbound labeled molecule to be cleared to background level; (c) determining the background level; and (d) detecting the labeled molecule such that detection of labeled molecule above the background level indicates the presence of a metastatic lesion.

In another preferred embodiment, the labeled molecule of the invention can be detected in a subject wherein the subject had been administered the labeled molecule at a sufficient time interval prior to detection to allow the labeled molecule to preferentially concentrate at metastatic lesions.

In specific embodiments the labeled molecule is labeled anti-uPAR antibody or fragments containing the uPAR binding domain or peptide mimetics of uPAR. In another specific embodiment, the labeled molecule is a peptide or derivative thereof that binds uPAR, for example, but not limited to, the peptides having the amino acid sequence of SEQ ID NO:1 (FIG. 1) and SEQ ID NO:2 (FIG. 2).

The principal of the invention is illustrated by working examples which demonstrate the biodistribution of uPAR in vivo, and show preferential accumulation of antibodies to uPAR at metastatic lesions in animal models.

4. BRIEF DESCRIPTION OF THE FIGURES

FIG. 1. Amino acid sequence of receptor binding domain of human uPA residues 7–33 (Appella et al., 1987, J. Biol. Chem. 262(10):4437–4440).

FIG. 2. Amino acid sequence of receptor binding domain of human uPA residues 12–32 (Appella et al., 1987, J. Biol. Chem. 262(10):4437–4440).

FIGS. 3A, B. Characterization of ruPAR IgG by immunofluorescence. (A) Mat B-III cells were grown to 70% confluency on glass slides and incubated with 10 μg/ml of preimmune rabbit IgG or (B) with 10 μg/ml of ruPAR IgG. Following incubation with a FITC conjugated anti-rabbit IgG secondary antibody (X20) the cells were analyzed for immunofluorescence.

Figure 4:
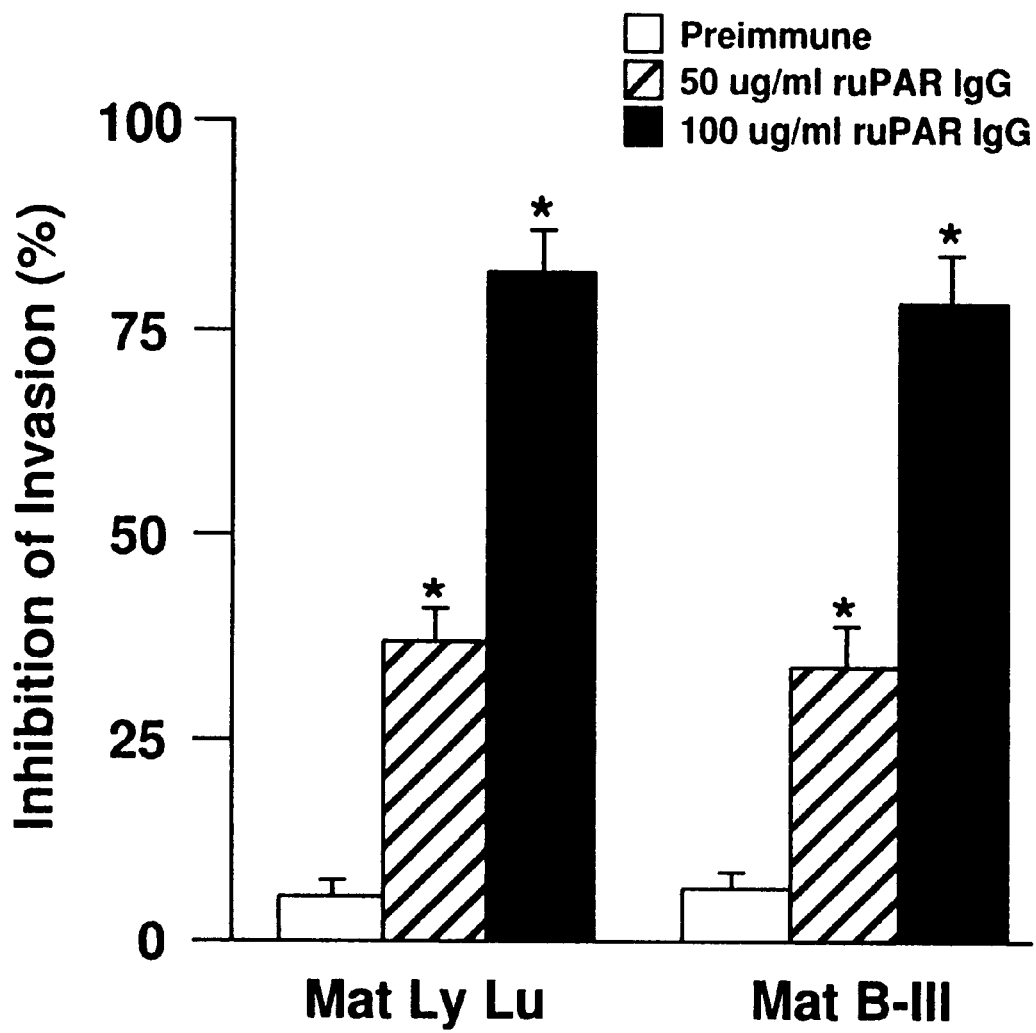

FIG. 4. Dose dependent inhibition of Mat Ly Lu and Mat B-III cell invasion by anti ruPAR IgG. Mat Ly Lu and Mat B-III cells were grown in culture and added to the upper compartment of a Boyden chamber with 50 or 100 μg/ml of ruPAR IgG. After 24 hours, the number of cells that migrated to the lower aspect of the Boyden chamber filter were counted. Percent inhibition of cell invasion was calculated by taking the number of cells that invaded following treatment with 50 or 100 μg/ml of preimmune IgG as 100%. Results are the mean ±SE of four such experiments. Significant inhibition in cell invasion from control cells are represented by asterisks (*P<0.05).

Figure 5B:
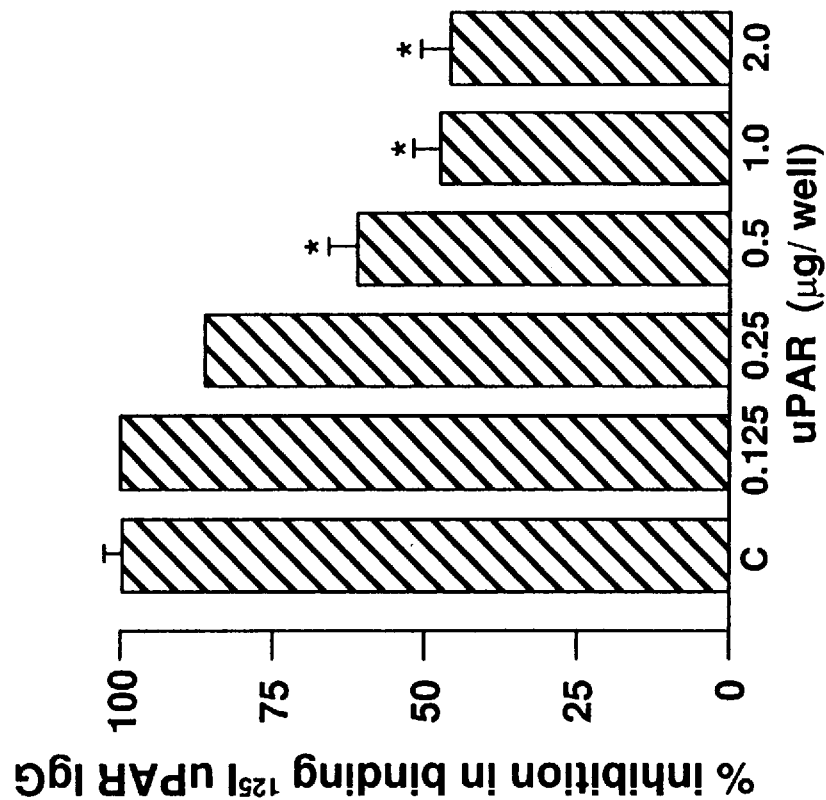
Figure 5A:
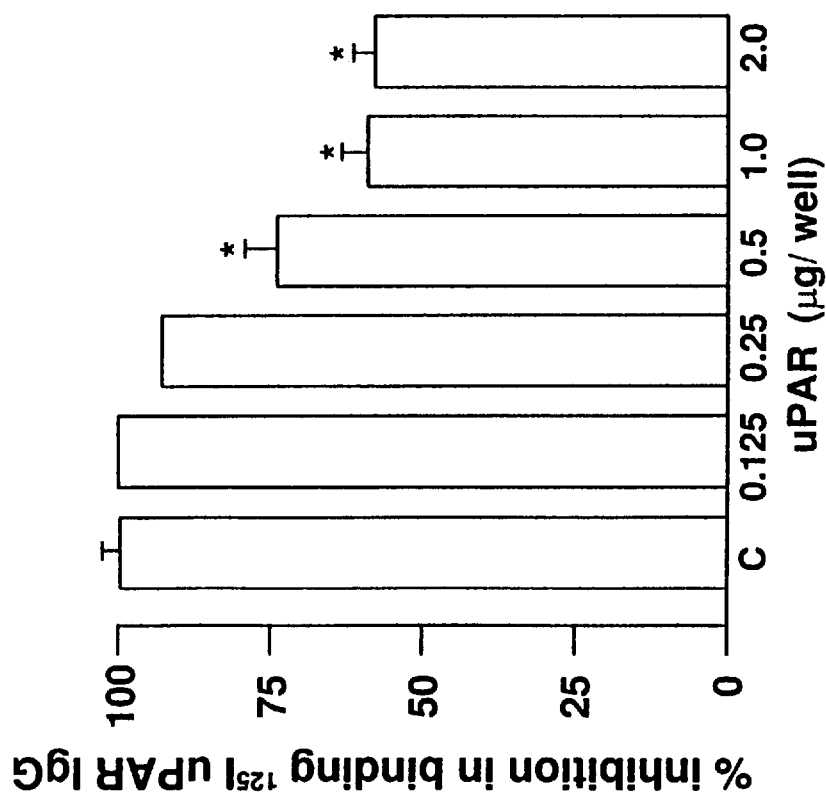

FIGS. 5A, B. Effect of ruPAR and uPAR IgG on $^{125}$I ruPAR IgG binding in Mat Ly Lu and Mat B-III-uPAR cells. (A) Mat Ly Lu and (B) Mat B-III-uPAR were incubated with $^{125}$I ruPAR-IgG, with or without increasing concentrations of ruPAR protein. The % change in $^{125}$I ruPAR-IgG binding after incubation with different concentrations of recombinant rat uPAR as compared to control cells is shown. Results are the mean ±SE of four experiments. Significant inhibition in binding from control cells are represented by asterisks (*P<0.05).

Figure 6:
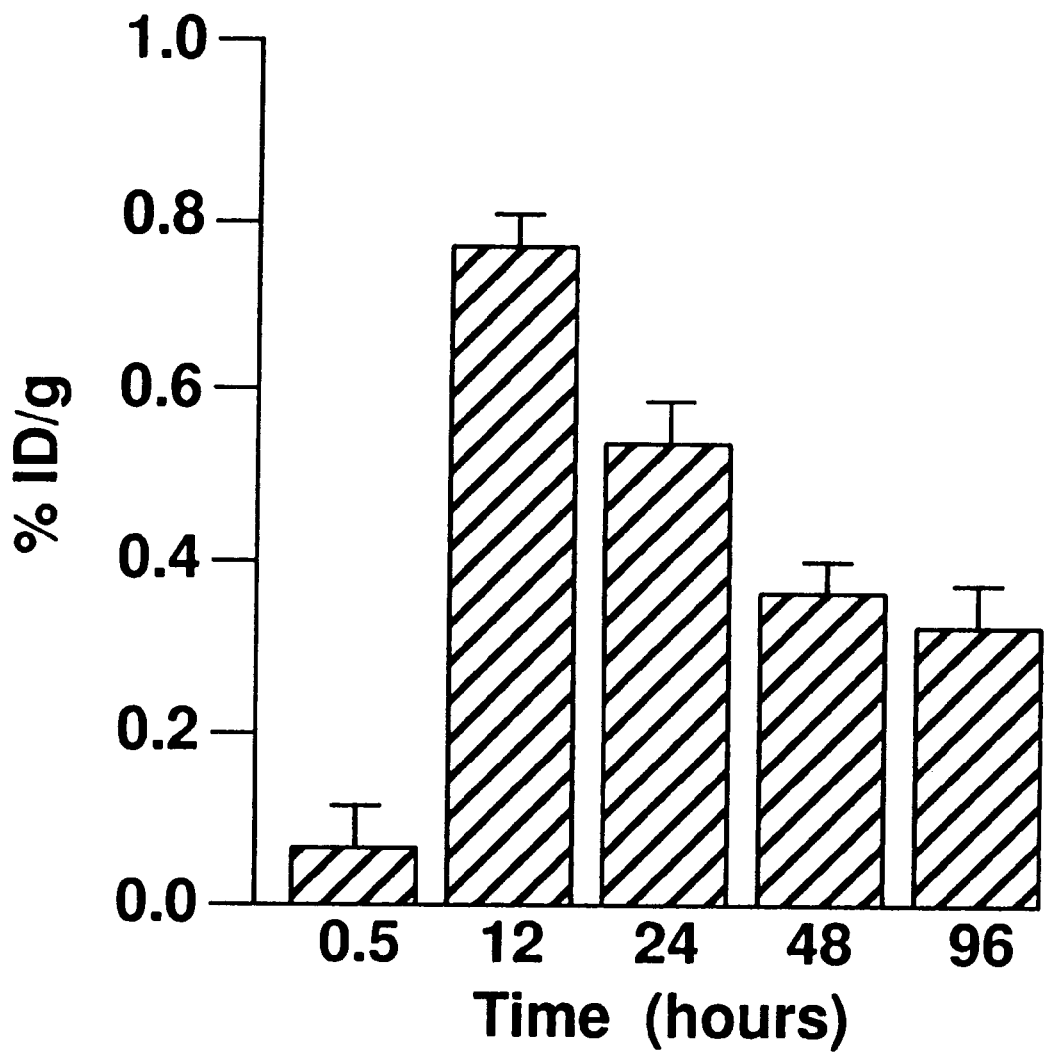

FIG. 6. Time course of $^{125}$I ruPAR IgG uptake by primary tumors in vivo. Uptake of radioactivity in Mat B-III-uPAR tumors in female Fischer rats was monitored at various time points after intravenous injection of $^{125}$I labeled pre-immune ruPAR IgG. Data represents the average % ID/g of 5 animals±SE of two such experiments.

Figure 7:
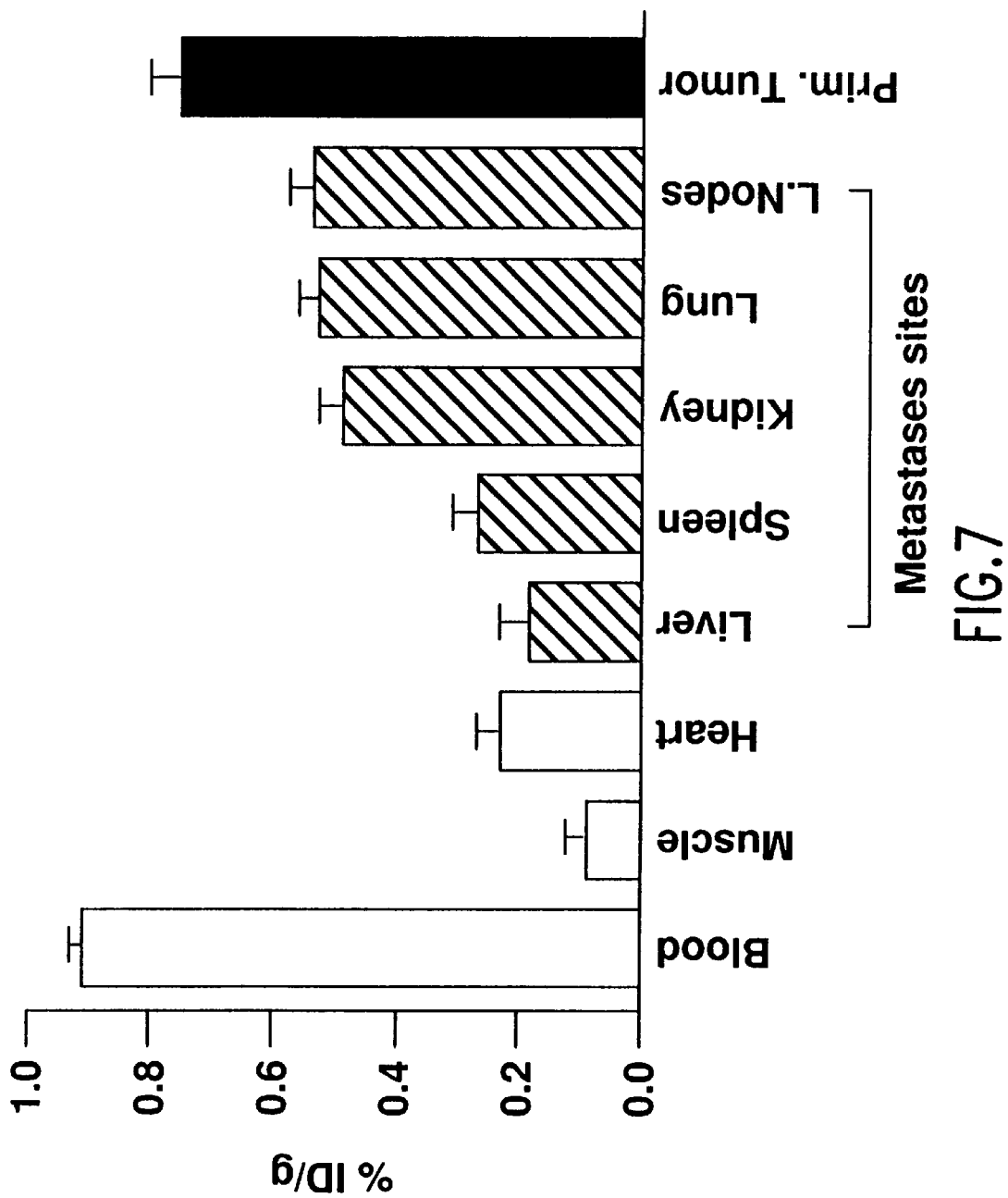

FIG. 7. Uptake of $^{125}$I labeled ruPAR IgG at primary and metastatic Mat B-III tumor sites. On day 10 post inoculation with Mat B-III-uPAR cells into Fischer rats, animals were injected with $^{125}$I labeled pre-immune or ruPAR IgG. After 12 hours, biodistribution of $^{125}$I ruPAR IgG in different normally unaffected tissues (adrenals, muscle, heart); sites of tumor metastases (liver, spleen, kidney, lungs, lymph nodes); and primary tumors, was determined. Results represent % ID/g of 6 animals in each group ±SE of three such experiments.

Figure 8:
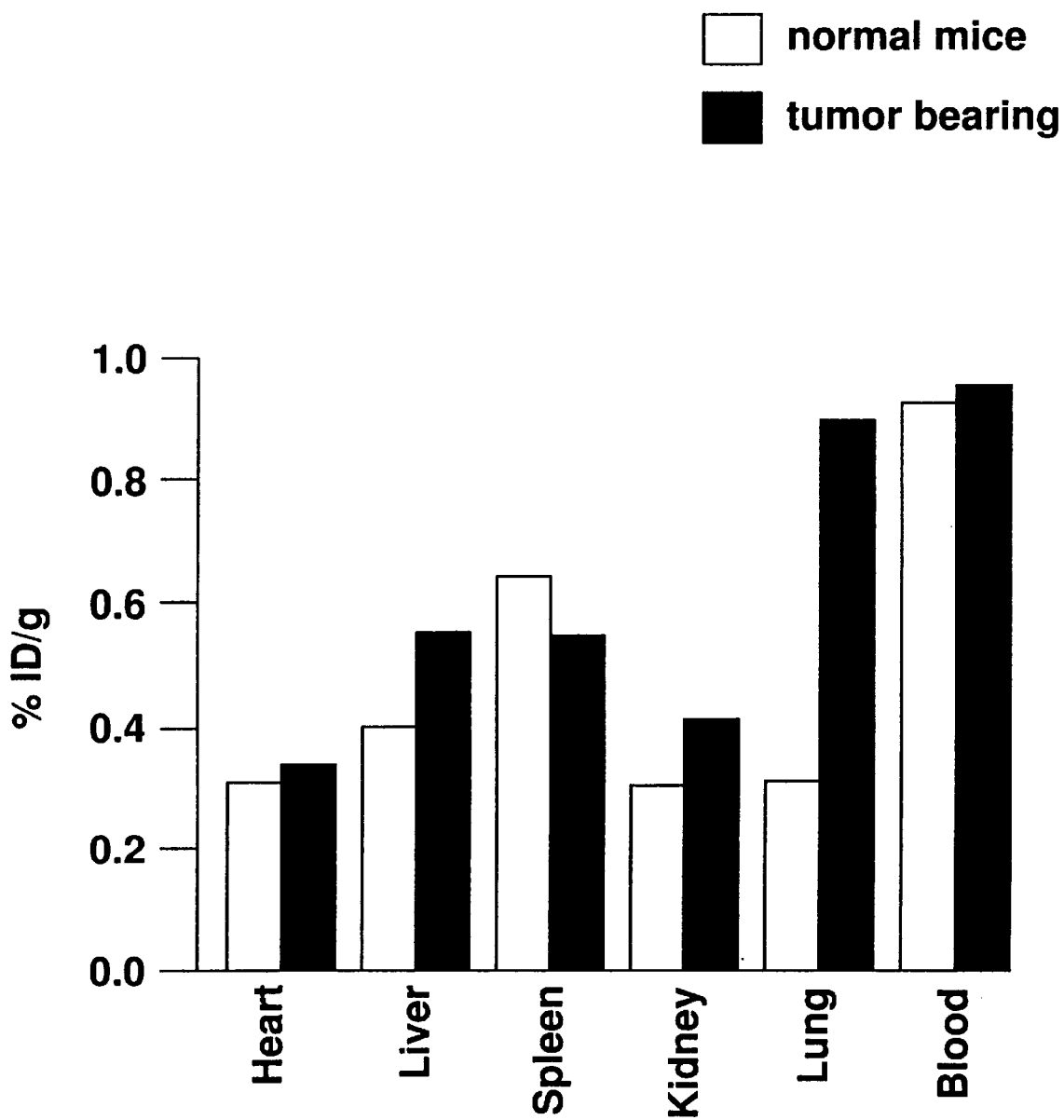

FIG. 8. Uptake of $^{125}$I labeled HuPAR IgG at primary tumors and metastatic lesions in tumor bearing mice. Tumor xenografts of human prostate cells were established in Balb/c nu/nu mice. Five weeks post inoculation with tumor cells, animals were injected with $^{125}$I labeled pre-immune huPAR IgG. After 12 hours, biodistribution of $^{125}$I huPAR IgG in different tissues was examined including: normal tissue (heart); sites of tumor metastases (liver, spleen, kidney, lungs, lymph nodes); and primary tumors was determined. The biodistribution was calculated and expressed as % of injected dose/gram of tissue (% ID/g).

Figure 9:
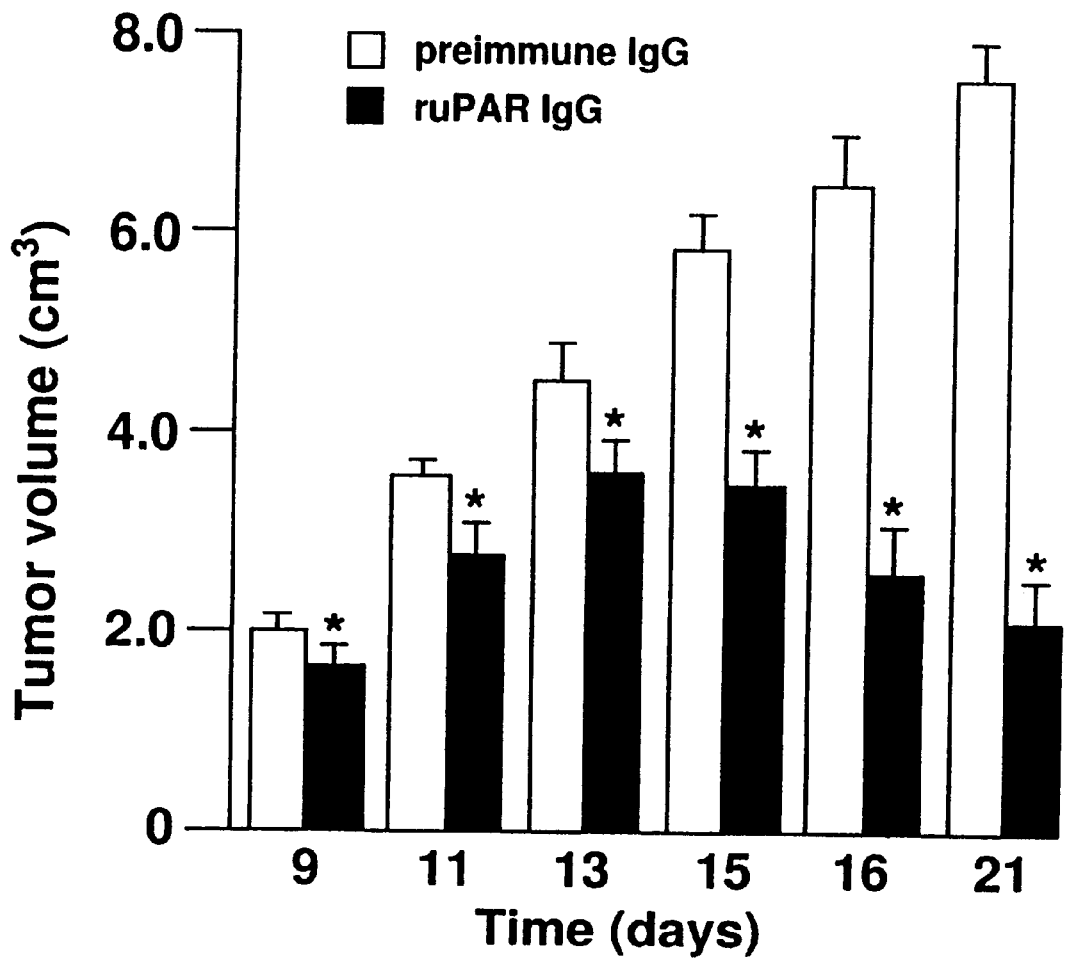

FIG. 9. Effect of anti-uPAR IgG on primary tumor volume in vivo. Mat B-III-uPAR rat mammary adenocarcinoma cells were implanted into the mammary fat pad of female Fisher rats. From day 1 to day 7 post tumor cell inoculation, animals received pre-immune rabbit IgG (50–100 μg/ml/day) or anti-ruPAR IgG (100 μg/day). For 2 to 3 weeks post tumor cell inoculation, primary tumor size was measured in two dimensions by calipers and tumor volume was calculated.

5. DETAILED DESCRIPTION OF THE INVENTION

The present invention relates to antibodies, derivatives and analogs thereto, peptides and peptide mimetics that specifically bind to a urokinase plasminogen activator receptor (uPAR). The usage of the term "a uPAR" indicates that even though the polypeptide portion of uPAR in a species may be the same for all uPARs, there is a plurality of uPARs. For example, the carbohydrate part of the mechanism of surface attachment of the uPAR may be different. Further, some cells, e.g., cancer cells, may have different uPARs.

The invention further relates to the use of molecules having binding specificity for uPAR for the detection, diagnosis, or monitoring in vivo, of metastases, preferably micrometastases. In one embodiment of the invention, the subject is injected with the molecule having binding specificity for uPAR. After a time sufficient to allow for distribution and accumulation in vivo, the subject can be imaged. A variety of methods can be used to detect accumulated labeled material in vivo, including but not limited to radioimaging techniques, e.g., X-ray, CAT scan, and magnetic resonance imaging (MRI), sonography, and positron emission tomography (PET).

5.1. UROKINASE RECEPTOR BINDING MOLECULES

Described herein are methods for the production of molecules capable of specifically recognizing one or more uPAR epitopes or epitopes of conserved variants or peptide fragments of a uPAR, including, but not limited to, antibodies, derivatives (including but not limited to fragments) and analogs thereof, and peptides and peptide mimetics.

Such uPAR binding molecules may be used, for example, in the detection of uPAR in a biological sample and may, therefore, be utilized as part of a diagnostic technique whereby subjects may be tested for abnormal levels of uPAR. According to one embodiment of the invention, a uPAR binding molecule specifically binds to the human uPAR.

5.1.1. ANTIBODIES TO uPAR, DERIVATIVES AND ANALOGS

Such uPAR binding molecules may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

Various procedures known in the art may be used for the production of polyclonal antibodies to a uPAR protein or fragment thereof. For the production of polyclonal antibody, various host animals can be immunized by injection with the native uPAR protein, or a synthetic version, or fragment thereof, including but not limited to rabbits, mice, rats, chickens, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a uPAR protein sequence, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089 and Winter, U.S. Pat. No. 5,225,539, which are incorporated herein by reference in their entirety.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against uPAR. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science, 246, 1275–1281) to allow rapid and easy identification of monoclonal Fab fragments with the desired specificity.

5.1.2. PEPTIDES, DERIVATIVES, ANALOGS, AND PEPTIDE MIMETICS

In an embodiment of the invention, uPAR binding molecules include peptides, derivatives and analogs thereof, and peptide mimetics. In particular embodiments of the invention, the peptides or peptide mimetics are selected to mimic the following sequences of human uPA:

VPSNCDCLNGGTCVSNKYFSNIHWCNC    (SEQ ID NO:1)

and

DCLNGGTCVSNKYFSNIHWCN    (SEQ ID NO:2).

In a specific embodiment, the methods of the invention use uPA derivatives and analogs, in particular uPA fragments and derivatives of such fragments, that comprise one or more domains of a uPA protein.

In another specific embodiment, the methods of the invention use a uPA protein, fragment, analog, or derivative which is expressed as a fusion, or chimeric protein product (comprising the protein, fragment, analog, or derivative joined via a peptide bond to a heterologous protein sequence (of a different protein)). A specific embodiment relates to a chimeric protein comprising a fragment of uPA of at least six amino acids.

Peptides, derivatives and analogs thereof, and peptide mimetics that specifically bind uPAR can be produced by various methods known in the art, including, but not limited to solid-phase synthesis or by solution (Nakanishi et al., 1993, Gene 137:51–56; Merrifield, 1963, J. Am. Chem. Soc. 15:2149–2154; Neurath, H. et al., Eds., *The Proteins*, Vol II, 3d Ed., p. 105–237, Academic Press, New York, N.Y. (1976). For example, a peptide corresponding to a portion of a uPA protein which comprises the desired domain or binding to a receptor, can be synthesized by use of a peptide synthesizer. Furthermore, if desired, nonclassical amino acids or chemical amino acid analogs can be introduced as a substitution or addition into a uPA sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

The uPA peptides may be isolated and purified by standard methods including chromatography (e.g., ion exchange, affinity, and sizing column chromatography), centrifugation, differential solubility, or by any other standard technique for the purification of peptides.

The functional properties may be evaluated using any suitable assay, including, but not limited to, competitive and non-competitive assay systems using techniques such as radioimmunoassays, ELISA (enzyme linked immunosorbent assay), "sandwich" immunoassays, immunoradiometric assays, in situ immunoassays (using colloidal gold, enzyme or radioisotope labels, for example), western blots, immunofluorescence assays, and immunoelectrophoresis assays, etc. For example, to select antibodies which recognize a specific domain of a uPAR, one may assay generated hybridomas for a product which binds to a uPAR fragment containing such domain. In one embodiment, antibody binding is detected by detecting a label on the antibody. Many means are known in the art for detecting binding in an immunoassay and are within the scope of the present invention.

The production and use of derivatives and analogs related to uPA are within the scope of the present invention. In a specific embodiment, the derivative or analog is functionally active, i.e., capable of exhibiting one or more functional activities associated with a full-length, wild-type uPA protein. As one example, such derivatives or analogs which have the desired antigenicity can be used, for example, in diagnostic immunoassays as described in Section 5.2. Derivatives or analogs of uPA can be tested for the desired activity by procedures known in the art, including but not limited to the assays described infra. In one specific embodiment, peptide libraries can be screened to select a peptide with the desired activity; such screening can be carried out by assaying, e.g., for binding to uPAR.

In particular, uPA derivatives can be made by altering uPA sequences by substitutions, additions or deletions that provide for functionally equivalent molecules. The uPA derivatives of the invention include, but are not limited to, those containing, as a primary amino acid sequence, all or part of the amino acid sequence of a uPA peptide including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of uPA include but are not limited to those peptides which are substantially homologous to uPA or fragments thereof.

Included within the scope of the invention are uPA protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc.

5.2. LABELING

Described herein are methods for detectably labeling molecules capable of specifically recognizing one or more uPAR epitopes or epitopes of conserved variants or peptide fragments of a uPAR. The labeling and detection methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

One of the ways in which the uPAR-specific antibody or peptide mimetic can be detectably labeled is by linking the same to an enzyme, such labeled molecules can be used in an enzyme immunoassay such as ELISA (enzyme linked immunosorbent assay). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibodies, derivatives and analogs thereof, and peptides include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

For use in the detection methods of the invention, the molecules are preferably labeled with a radioisotope, including but not limited to: $^{125}$I, $^{131}$I, or $^{99m}$Tc. Such peptides and antibodies can be detected in in vitro assays using a radioimmunoassay (RIA) or radioprobe. The radioactive isotope can be detected by such means as the use of a gamma counter or a scintillation counter or by autoradiography.

It is also possible to label the antibodies, derivatives and analogs thereof, and peptides with a fluorescent compound. When the fluorescently labeled peptide is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibodies, derivatives and analogs thereof, and peptides can also be detectably labeled using fluorescence emitting metals such as $^{152}$Eu, or others of the lanthanide series. These metals can be attached to the antibodies, derivatives and analogs thereof, and peptides using such metal chelating groups as diethylenetriaminepentacetic acid (DTPA) or ethylenediaminetetraacetic acid (EDTA).

The antibodies, derivatives and analogs thereof, and peptides also can be detectably labeled by coupling to a chemiluminescent compound. The presence of the chemiluminescent-tagged peptides are then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibodies, derivatives and analogs thereof, and peptides of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.3. METHODS OF ADMINISTRATION

The molecules that are determined to specifically bind uPAR can be administered to a patient at diagnostically effective doses to detect metastases. A diagnostically effective dose refers to that amount of the molecule sufficient to target a diagnostic to a cell containing uPAR on its surface such that the cell can be detected using methods commonly available in the art, e.g., as described in Section 5.4.1 supra.

5.3.1. EFFECTIVE DOSE

Toxicity and diagnostic efficacy of such molecules can be determined by standard pharmaceutical procedures in cell cultures or experimental animals, e.g., for determining the $LD_{50}$ (the dose lethal to 50% of the population).

The data obtained from the cell culture assays and animal studies can be used in formulating a range of dosage for use in humans. For example, the animal model systems described in Examples 7 and 8 can be used to assay for doses effective to visualize metastatic lesions using the labeled molecules. The dosage of such compounds lies preferably within a range of circulating concentrations with little or no toxicity. The precise dose to be employed in the formulation will depend on the route of administration and the seriousness of the disease, and should be decided according to the judgment of the practitioner and each patient's circumstances. However, suitable dosage ranges for intravenous administration are generally about 1.0 to 20 micrograms of compound per kilogram body weight. Levels in plasma may be measured, for example, by high performance liquid chromatography.

5.3.2. FORMULATIONS AND USE

Pharmaceutical compositions for use in accordance with the present invention may be formulated in conventional manner using one or more physiologically acceptable carriers or excipients.

Methods of administration include but are not limited to intravenous, subcutaneous, intraperitoneal, and intradermal routes. Administration can be systemic or local. In a specific embodiment, it is desirable to administer the pharmaceutical compositions of the invention locally by direct injection at the site (or former site) of a malignant tumor or metastatic tissue.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The invention also provides a pharmaceutical pack or kit comprising one or more containers filled with one or more of the ingredients of the pharmaceutical compositions of the invention.

5.4. DIAGNOSIS AND IMAGING OF METASTASIS

Labeled antibodies, derivatives and analogs thereof, and peptides and peptide mimetics which specifically bind to a uPAR can be used for diagnostic purposes to detect, diagnose, or monitor metastases. In a preferred embodiment, the molecules of the invention can be used for diagnostic purposes to detect, diagnose, or monitor micrometastases.

In one embodiment, metastases are detected in patient samples. In a preferred embodiment, metastases are detected in the patient. The patient is an animal and is preferably a human.

In an embodiment, diagnosis is carried out by: a) administering to a subject an effective amount of a labeled molecule which specifically binds to a urokinase receptor; b) delaying detecting for a time interval following the administering for permitting the labeled molecule to preferentially concentrate in any metastatic lesions in the subject and for unbound labeled molecule to be cleared to background level; c) determining background level; and d) detecting the labeled molecule in the subject, such that detection of labeled molecule above the background level indicates the presence of a metastatic lesion. Background level can be determined by various methods including: measuring the amount of labeled molecule in tissue which does not normally express uPAR, e.g., muscle, either in the subject being diagnosed or in a second subject not suspected of having metastatic tissue; or comparing the amount of labeled molecule detected to a standard value previously determined for a particular system.

Depending on several variables, including the type of label used and the mode of administration, the time interval following the administering for permitting the labeled molecule to preferentially concentrate in any metastatic lesions in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the metastasis is carried out by repeating the method for diagnosing the metastasis, for example, one month after initial diagnosis, six months after initial diagnosis, one year after initial diagnosis, etc.

5.4.1. METHODS OF DETECTION AND IMAGING

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include but are not limited to: computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument.

5.5. THERAPEUTIC USES

The invention provides for treatment of various cancers by administration of a therapeutic compound (termed herein "Therapeutic"). Such Therapeutics include but are not limited to: antibodies, derivatives and analogs thereof, and peptides and peptide mimetics which specifically bind to a uPAR (as described hereinabove). For an illustrative example, see section 9 and Table 1.

In a preferred embodiment, a cytotoxic or cytostatic compound, including but not limited to: saporin, A-chain ricin, A-chain cholera toxin, an antibiotic, an antimetabolite, is coupled to the Therapeutic.

6. EXAMPLE: ANTIBODIES TO uPAR BLOCK INVASION OF TUMOR CELLS THROUGH BASEMENT MEMBRANE

The experiments described below demonstrate the ability of ruPAR antibody to specifically bind uPAR, and to block cancer cell invasion through basement membrane.

6.1. MATERIALS AND METHODS

Cell and Cell Culture The Dunning R3227 Mat Ly Lu rat prostate cancer cell line was obtained from Dr T. J. Isaacs (Johns Hopkins School of Medicine, Baltimore, Md). Rat breast cancer cell line Mat B-III was obtained from American Type Culture Collection (Rockville, Md). Mat B-III cells overexpressing uPAR (Mat B-III-uPAR) were developed as described in Xing and Rabbani, 1996, Int. J. Cancer 67: 423–429, incorporated herein by reference in its entirety. Cells were maintained in RPMI 1640 or in McCoy's 5A medium supplemented with 10% fetal bovine serum (FBS), 2 mM glutamine, 100 Units/ml penicillin and 100 ng/ml streptomycin (Gibco, Grand Island, N.Y). Cells were grown under standard tissue culture conditions at 37° C. in a humidified atmosphere containing 5% $CO_2$ in 75 $cm^2$ flasks or six well tissue culture plates (Archbarou et al., 1994, Cancer Res. 54:2372–2377; Xing and Rabbani, 1996, Int. J. Cancer 67: 423–429).

Anti-rat uPAR Antibody

Full length cDNA encoding rat (r) uPAR was isolated from a rat osteoblast cDNA library (Rabbani et al., 1994, FEBS Letters 338:69–74). A Pst I restriction digest of ruPAR cDNA resulted in the release of a 271 bp cDNA encoding amino acids 25–114 of rat uPAR which was subcloned in the sense orientation into the expression vector pTrcHis A (Invitrogen, San Diego, Calif.). Orientation and in frame insertion of ruPAR cDNA was further confirmed by nucleotide sequence analysis. Recombinant ruPAR protein was expressed and then purified on a commercially available Protein G column according to manufacturer's instructions. Amino acid sequence of recombinant ruPAR was confirmed using PI 2090E Integrated microsequencing system (Beckman Instruments, Mississauga, ONT.) at Sheldon Biotechnology Centre, McGill University.

Rabbits were immunized with ruPAR at multiple (8–10) sites subcutaneously using Freunds incomplete adjuvant (Sigma, St. Louis, Mo.) at 4 week intervals and bled 10 days after each immunization. The antiserum employed in this study was obtained after the third booster. Immunoglobulin fraction (IgG) was purified from antiserum against ruPAR using protein A Sepharose CL-4B (Pharmacia, LKB Bale D'Urfe, Quebec) according to the manufacturer's instructions.

Indirect Immunofluorescence

The ability of this species specific ruPAR IgG to recognize endogenous ruPAR protein was examined in Mat Ly Lu and in Mat B-III cancer cells. Cells ($5 \times 10^4$ cells) were plated in Lab Tek tissue culture chambers (Nunc, Naperville, Ill.) and allowed to grow to 70–80% confluence. Cells were then incubated with 30% goat serum (Sigma, St. Louis, Mo.) for 1 hour at room temperature and washed with PBS containing 1% BSA. Sequentially, cells were incubated with primary rabbit IgG to ruPAR and goat-anti-rabbit IgG conjugated to fluorescein isothiocyanate (FITC). Pictures were taken at 25×magnification using a Zeiss MC-63 microscope.

Matrigel Invasion And Receptor Binding Assay

The capacity of ruPAR IgG to block the invasiveness of Mat Ly Lu and Mat B-III-uPAR cells was tested by two-compartment Boyden chambers (Transwell, Costar, USA) and basement membrane Matrigel (Becton Dikinson Labware) (Xing and Rabbani, 1996, Int. J. Cancer 67: 423–429). Eight (8) μm pore sized polycarbonate filters were coated with basement membrane Matrigel (45 μg/filter) and dried under a tissue culture hood. Matrigel was then reconstructed by adding 0.1 ml serum-free culture medium to the upper chamber and incubating for 90 min. After removal of medium, cells (5×10$^4$) in 0.1 ml of culture medium supplemented with 10 μg/ml of anti-ruPAR IgG or 10 μg/ml of preimmune IgG were added to the upper chamber and placed in a lower chamber pre-filled with 1.0 ml of serum free medium supplemented with 5 μg/ml fibronectin (Sigma, St Louis, Mo.), and incubated at 37° C. for 24 hours. At the end of incubation, medium was removed and cells were fixed in 2% paraformaldehyde, 0.5% glutaraldehyde in 0.1 M phosphate buffer pH 7.4 at room temperature for 30 min. After washing with PBS all filters were stained with 0.05% toluidine blue. Filters were mounted on glass slides and cells were examined under a light microscope. Ten fields under 100 × magnification were randomly selected and mean cell number calculated.

One hundred micrograms of pre-immune or ruPAR IgG were labeled with 1 MCi of $^{125}$I using the chloramine T method, yielding a specific activity of 0.8–1.0 μCi/μg protein (Rabbani et al., 1992, J. Biol. Chem. 267:14151–14156). The free $^{125}$I was separated from the labeled IgGs on a Sephadex G-25 gel filtration column (Pharmacia, Uppsala, Sweden) which was equilibrated and eluted with phosphate buffered saline containing 0.1% bovine serum albumin (BSA).

Mat Ly Lu and Mat B-III-uPAR cells were plated in 24 well plates (30,000 and 80,000 cells respectively) and allowed to grow to 70% confluency. Following serum deprivation for one hour, the cells were treated with 50mM glycine and 10 mM NaCl PH.0 for 3 min. The cells were then incubated for 1 hour at 37° C. in a final volume of 300 μl containing serum free medium, 1 mg/ml BSA, 20 mM Hepes PH 7.4, $^{125}$ruPAR IgG (100,000 cpm), with or without increasing concentrations of competitor (ruPAR protein). The binding reaction was stopped by washing four times with ice cold Hanks balanced salt solution, and the cells removed with 1 ml of 0.6N NaOH for subsequent determination of radioactivity (Rabbani et al., 1992, J. Biol. Chem. 267:14151–14156; Xing and Rabbani, 1996, Int. J. Cancer 67: 423–429).

Statistical Analysis

Statistical analysis was done by one way analysis of variance or by Student's t test.

6.2. RESULTS

Characterization of Anti Rat uPAR IgG

Figure 3B:
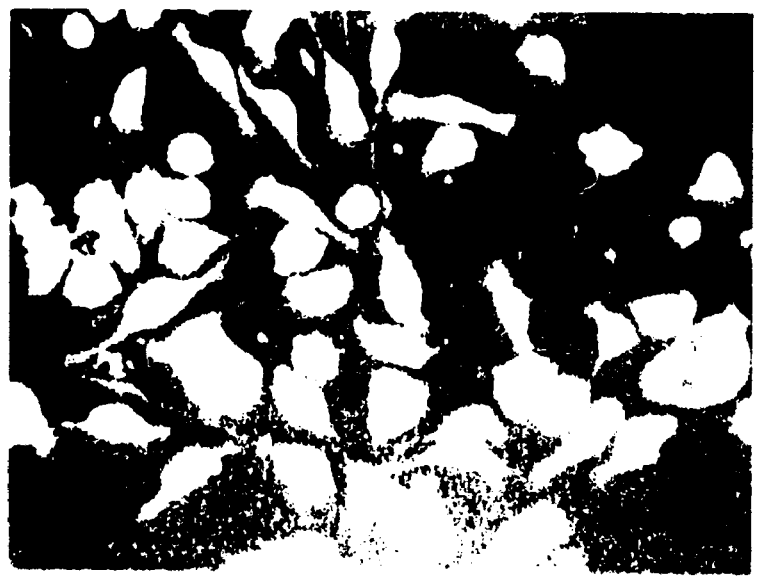

The ability of ruPAR IgG to recognize the cell surface receptor for uPA, abundantly expressed by MatB-III cells, was examined by immunofluorescence. Control cells incubated with 10 μg/ml of preimmune rabbit IgG failed to show any binding to ruPAR as assessed by immunofluorescence (FIG. 3A). In contrast to this, 10 μg/ml of ruPAR IgG showed fluorescence reaction in MatB-III-uPAR cells (FIG. 3B). This antibody-receptor complex was seen on the cell surface where uPAR is reported to be expressed. Similar results were obtained with ruPAR IgG in Mat Ly Lu cells.

Effect of Anti ruPAR IgG on Tumor Cell Invasion In Vitro

The role of the $NH_2$-terminal region of uPAR in ligand binding and in cell invasiveness was further examined in Mat Ly Lu and in MatB-III-uPAR cells using Matrigel invasion assay. After 24 hrs of incubation, both Mat Ly Lu and MatB-III cells were able to penetrate the basement membrane. Incubation of these cells in the presence of 50–100 μg/ml of preimmune rabbit IgG did not cause any significant inhibition in the invasive capacity of these rat prostate and breast cancer cells (FIG. 4). In contrast, the number of cells invading through the basement membrane was significantly reduced as compared to control cells treated with preimmune rabbit IgG (FIG. 4). These effects were found to be dose dependent where 50 μg/ml or 100 μg/ml of IgG inhibited cell invasion by 40% and 80% respectively.

7. EXAMPLE: RECEPTOR BINDING AND BIO-DISTRIBUTION OF $^{125}$I RAT uPAR IgG

The binding specificity and biodistribution of labeled ruPAR antibody in vivo is described in the subsections below. These results showed that labeled anti-uPAR antibody accumulated in tissues that are common sites of tumor metastases before metastases could be detected macroscopically. These experiments also demonstrated that unlabeled ruPAR inhibits binding of $^{125}$I ruPAR IgG in a dose dependent manner. Labeled ruPAR antibody was observed to concentrate in primary tumors in a time dependent manner. In addition, the ability of ruPAR antibody to bind preferentially in the primary tumor and, surprisingly, in metastatic lesions was demonstrated.

7.1. MATERIALS AND METHODS

Animal Protocols

Inbred female Fischer rats weighing 200–250 g were obtained from Charles River, Inc. (St. Constant, Canada). Before inoculation, Mat B-III-uPAR tumor cells grown in serum-containing medium were washed with Hank's buffer and trypsinized for five minutes. Cells were then collected in Hank's buffer and centrifuged at 1500 rpm for 5 min. Cell pellets (1×10$^6$ cells) were resuspended in 200 μl saline and injected using one ml insulin syringes into the mammary fat pad of rats anesthetized with ethanol/Somnotal (MTC Pharmaceuticals, Cambridge, Ontario).

For biodistribution studies, on day 10 post tumor cell inoculation, animals were injected with $^{125}$I labeled preimmune or ruPAR IgG (25 μg, 25 μCi) via tail vein injection. In a separate experiment, on day 15 post tumor cell inoculation, animals were injected via the tail vein with the labeled material. Animals were sacrificed 0.5–96 hours after injection. Primary tumors from the site of tumor cell inoculation (mammary fat pad) were removed and counted for radioactivity. Alteratively, 12 hrs after injection of radiolabelled preimmune or ruPAR IgG, primary tumors and various organs (heart, liver, spleen, lungs, kidneys and lymph nodes) were removed and total radioactivity uptake in these organs was monitored using a gamma counter. Biodistribution of $^{125}$I ruPAR IgG was calculated and expressed as % of injected dose/gram tissue (% ID/g) of $^{125}$I ruPAR IgG-$^{125}$I labeled pre-immune IgG (Folli et al., 1994, Cancer Res. 54:2643–2649).

7.2. RESULTS

Receptor Binding and Biodistribution of $^{125}$I Labeled ruPAR IgG

The ability of ruPAR IgG to interfere with the functional ability of uPAR was evaluated in a receptor binding assay.

Total binding of $^{125}$I ruPAR IgG to Mat Ly Lu and Mat B-III-uPAR cells was determined. Addition of different concentrations (0.1–2.0 mg) of unlabeled recombinant rat uPAR inhibited the binding of 125I ruPAR IgG in a dose dependent manner in both Mat Ly Lu (FIG. 5A) and Mat B-III (FIG. 5B) cells. A similar dose dependent decrease in $^{125}$I ruPAR IgG binding was seen following addition of different concentrations of unlabeled ruPAR IgG as compared to pre-immune rabbit IgG to their tumor cells.

To examine the specificity and time course of $^{125}$I ruPAR IgG, both pre-immune and ruPAR IgG were labeled with $^{125}$I and injected via the tail vein into Mat B-III-uPAR tumor bearing female Fischer rats (at 15 days post tumor cell inoculation). Animals were sacrificed at timed intervals (0.5–96 hr). Primary tumors were removed and counted for $^{125}$I uptake. % ID/g of ruPAR IgG was highest in tumor bearing animals after 12 hr of $^{125}$I IgG injection after which time the % ID/g declined for up to 96 hr (FIG. 6).

Tumor bearing animals (10 day post tumor cell inoculation) were injected via the tail vein with $^{125}$I uPAR IgG and sacrificed 12 hours post injection with the labeled uPAR material. Accumulation of label was examined in: (1) normal tissues (muscle, heart); (2) tissues that are common sites of tumor metastases (liver, spleen, kidney, lungs, lymph nodes); and (3) primary tumors. Minimal amounts of radioactivity were seen in muscle, whereas the levels of $^{125}$I were slightly higher in the heart due to the presence of blood which showed high radioactivity uptake. In contrast to this, significantly higher levels of % ID/g of ruPAR IgG were seen in liver, spleen, kidney, lungs, lymph nodes and in the primary tumor (FIG. 7).

Although labeled material was detected in primary tumor and metastatic lesions of animals sacrificed on day 10 post tumor cell inoculation (FIG. 7), no macroscopic metastases were observed. However, macroscopic tumor metastases were observed in animals sacrificed at day 15 post tumor cell inoculation. These results suggest that the specific uptake of $^{125}$I ruPAR IgG by Mat B-III-uPAR tumor cells, already present at these sites on day 10, later developed into macroscopic metastases by day 15.

8. EXAMPLE: BIODISTRIBUTION OF $^{125}$I HUMAN uPAR IgG

The following example demonstrates the ability of $^{125}$I human (h) uPAR IgG to recognize cell surface uPAR and preferentially concentrate in primary tumor and metastatic lesions in vivo.

8.1. MATERIALS AND METHODS
Human uPAR IgG Radiolabelling

The monoclonal human uPAR IgG (#3936, American Diagnostica Inc., Greenwich, Conn.) or non-specific mouse IgG were labelled using the Iodogen method yielding a specific activity of 0.6–0.9 mCi/mg. Briefly, 100 µg of IgG was added to a vessel precoated with 10 µg of Iodogen (Pierce Chemical Co., Rockford, Ill.) according to the manufacturer's instructions. The reaction was allowed to proceed for 15 minutes at room temperature. The free $^{125}$I was separated from the labelled IgGs using a Sephadex G25 gel filtration column (Pharmacia, Uppsula, Sweden) preequilibrated with phosphate buffered saline (PBS) containing 0.1% bovine serum albumin (BSA).

In vivo Biodistribution Studies

Tumor xenografts were established in 4–6 week old nude (Balb/c nu/nu) mice by subcutaneous injection of $2 \times 10^6$ prostate cancer cells (PC-3) per mouse. Prior to injection, the cells grown in serum containing medium were washed with HBSS and trypsinized for 5 minutes. Cells were then collected in medium and centrifuged at 1500 rpm for 5 minutes and resuspended in 200 µl saline.

Five weeks following tumor cell inoculation, the $^{125}$I labeled IgGs were injected intravenously via the lateral tail vein, into the tumor bearing mice. The animals were sacrificed after 12–24 hours, and the primary tumor and various organs (heart, liver, spleen, lungs, kidney, lymph nodes, and blood) were removed. Total radioactivity was determined using a gamma counter. The biodistribution was calculated and expressed as % of injected dose/gram of tissue (% ID/g).

8.2. RESULTS

To examine the specificity of huPAR IgG, pre-immune IgG and the monoclonal human uPAR antibody, 3936, were labeled with $^{125}$I and injected into the tail vein of normal Balb/c nu/nu mice and Balb/c nu/nu mice bearing tumor xenografts of human prostate cells (PC-3).

The % ID/g of $^{125}$I huPAR IgG in (1) normal tissue (heart); (2) tissues that are common sites of metastases (liver, spleen, kidney, lungs, lymph nodes); and (3) primary tumors was examined. The levels of radioactivity were slightly high in the heart due to the presence of blood which showed a high intake of the radioactive molecule (FIG. 8A). In contrast, significantly higher levels of % ID/g were observed in the primary tumor and in the metastic tissues, particularly in the lung.

9. EXAMPLE: THERAPEUTIC EFFECTS OF uPAR ON TUMOR BEARING ANIMALS

The following example demonstrates the ability of anti-uPAR IgG to inhibit the growth rate of primary tumors and inhibit formation and growth of metastatic lesions.

9.1. MATERIALS AND METHODS
Animal Protocols

Inbred female Fischer rats weighing 200–250 g were obtained from Charles River, Inc. (St. Constant, Canada). Before inoculation, Mat B-III-uPAR tumor cells grown in serum-containing medium were washed with Hank's buffer and trypsinized for five minutes. Cells were then collected in Hank's buffer and centrifuged at 1500 rpm for 5 min. Cell pellets ($1 \times 10^6$ cells) were resuspended in 200 µl saline and injected using one ml insulin syringes into the mammary fat pad of rats anesthetized with ethanol/Somnotal (MTC Pharmaceuticals, Cambridge, Ontario).

Tumor bearing animals were injected with 50–100 µg/day of ruPAR IgG subcutaneously into the mammary fat pad from day 1 to day 7 post tumor cell inoculation. Control groups of tumor-bearing animals received either normal saline or 50–100 µg/day of preimmune rabbit IgG as control.

All animals were monitored for the development of tumors for 2–3 weeks post tumor cell inoculation. Tumor size in control and experimental animals was measured in two dimensions by calipers and tumor volume was calculated (Haq et al., 1993, J. Clin. Invest. 91:2416–2422). Control animals receiving pre-immune IgG and experimental animals injected with ruPAR IgG were sacrificed on day 10 or on day post tumor cell inoculation and evaluated for the presence of macroscopic metastases in various tissues.

9.2. RESULTS
Effect of Anti-ruPAR IgG on Tumor Volume

The ability of anti-ruPAR IgG to inhibit the growth rate of primary tumors was evaluated. Injection of pre-immune rabbit IgG into tumor bearing animals did not result in any significant difference in tumor growth. In contrast, injection of anti ruPAR IgG from day 1 to day 7 post tumor cell inoculation resulted in a significant decrease in tumor volume in these experimental animals (FIG. 9). This decrease in tumor volume was more pronounced in the later stages (day 15–day 21), when control animals continued to show a linear increase in tumor growth, while experimental animals receiving ruPAR IgG not only showed a decrease in tumor volume but also demonstrated a regression in tumor growth as compared to earlier stages (day 9–day 14) of tumor development (FIG. 9).

Effect of ruPAR IgG on Tumor Metastasis

To determine the effects of ruPAR IGG on tumor metastasis, control tumor bearing animals injected with preimmune rabbit IgG and experimental animals receiving ruPAR IgG were sacrificed at day 15 post tumor cell inoculation. Control animals reproducibly developed large macroscopic tumor metastases to axillary, retroperitoneal, and mesenteric lymph nodes. Evidence of occasional tumor metastasis was also seen in liver and spleen (Table 1). In contrast, tumor bearing animals receiving ruPAR IgG showed significantly smaller metastatic foci at retroperitoneal and mesenteric lymph nodes, without any evidence of tumor metastasis in liver or spleen (Table 1).

TABLE 1

EFFECT OF ANTI-RAT uPAR ON TUMAR METASTASES

|  | Preimmune IgG | ruPAR IgG |
|---|---|---|
| Axillary Lymph Nodes | 2 ± 1 | 1 ± 1 |
| Retroperitoneal Lymph nodes | 3 ± 2 | 1 ± 1 |
| Mesenteric Lymph nodes | 3 ± 1 | 1 ± 1 |
| Lungs | 1 ± 1 | 0 |
| Liver | 1 ± 1 | 0 |
| Spleen | 1 ± 1 | 0 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method for detecting one or more metastatic lesions comprising:
   a) administering to a subject an effective amount of a labeled molecule which specifically binds to a urokinase plasminogen activator receptor;
   b) delaying detecting for a time interval following the administering for permitting the labeled molecule to preferentially concentrate at any metastatic lesion in the subject and for unbound labeled molecule to be cleared to a background level; and
   c) detecting the labeled molecule in the subject, wherein detection of the labeled molecule above the background level indicates the presence of a metastatic lesion.

2. The method of claim 1 in which the subject is a human.

3. The method of claim 1 in which the molecule is an antibody to a urokinase plasminogen activator receptor or a portion of said antibody containing the urokinase plasminogen activator receptor binding domain.

4. The method of claim 1 in which the molecule is a humanized antibody.

5. The method of claim 1 in which the molecule comprises the amino acid sequence depicted in FIG. 1 (SEQ ID NO:1) or FIG. 2 (SEQ ID NO:2).

6. The method of claim 1 in which the labeled molecule is labeled with a radioisotope.

7. The method of claim 1 in which the labeled molecule is detected in vivo.

8. The method of claim 1 in which the time interval is 6 hours to 48 hours.

9. The method of claim 1 in which the labeled molecule is administered intravenously.

10. The method of claim 1 which further comprises repeating steps (a) through (c) at monthly intervals.

11. A method for detecting one or more metastatic lesions in a subject, comprising imaging said subject at a time interval after administration to said subject of an effective amount of a labeled molecule which specifically binds to a urokinase plasminogen activator receptor, said time interval being sufficient to permit the labeled molecule to preferentially concentrate at any metastatic lesion in said subject and for unbound labeled molecule to be cleared to background level, wherein detection of the labeled molecule above the background level indicates the presence of a metastatic lesion.

12. The method of claim 11 in which the subject is a human.

13. The method of claim 11 in which the molecule is an antibody to a urokinase plasminogen activator receptor or a portion of said antibody containing the urokinase plasminogen activator receptor binding domain.

14. The method of claim 11 in which the molecule is a humanized antibody.

15. The method of claim 11 in which the molecule comprises the amino acid sequence depicted in FIG. 1 (SEQ ID NO:1) or FIG. 2 (SEQ ID NO:2).

16. The method of claim 11 in which the labeled molecule is labeled with a radioisotope.

17. The method of claim 11 in which the time interval is 6 hours to 48 hours.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 27 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

```
Val Pro Ser Asn Cys Asp Cys Leu Asn Gly Gly Thr Cys Val Ser Asn
 1               5                  10                  15

Lys Tyr Phe Ser Asn Ile His Trp Cys Asn Cys
                20                  25
```

(2) INFORMATION FOR SEQ ID NO:2:

(i) SEQUENCE CHARACTERISTICS:
      (A) LENGTH: 21 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:2:

```
Asp Cys Leu Asn Gly Gly Thr Cys Val Ser Asn Lys Tyr Phe Ser Asn
 1               5                  10                  15

Ile His Trp Cys Asn
                20
```